(12) United States Patent
Cheon et al.

(10) Patent No.: US 7,279,264 B2
(45) Date of Patent: Oct. 9, 2007

(54) DYES AND USE THEREOF IN THERMAL IMAGING MEMBERS AND METHODS

(75) Inventors: Kap-Soo Cheon, Shrewsbury, MA (US); Peter K. Chu, Acton, MA (US); Michael P. Filosa, Medfield, MA (US); Stephen J. Telfer, Arlington, MA (US)

(73) Assignee: Zink Imaging, LLC, Waltham, MA (US)

(*) Notice: Subject to any disclaimer, the term of this patent is extended or adjusted under 35 U.S.C. 154(b) by 133 days.

(21) Appl. No.: 10/789,566

(22) Filed: Feb. 27, 2004

(65) Prior Publication Data

US 2004/0204317 A1    Oct. 14, 2004

Related U.S. Application Data

(60) Provisional application No. 60/451,208, filed on Feb. 28, 2003.

(51) Int. Cl.
    *G03F 7/00* (2006.01)
(52) U.S. Cl. .................. 430/270.1; 430/330; 430/311; 430/944; 430/945; 430/348; 430/843; 549/223; 503/218
(58) Field of Classification Search ............ 430/270.1, 430/944, 945, 348, 343, 311, 330; 549/223; 503/218
    See application file for complete search history.

(56) References Cited

U.S. PATENT DOCUMENTS

| | | | |
|---|---|---|---|
| 4,232,552 A | 11/1980 | Hof et al. ..................... 73/356 |
| 4,641,147 A * | 2/1987 | Sakura et al. ................ 347/174 |
| 5,278,031 A | 1/1994 | Boggs et al. ................ 430/348 |
| 5,401,619 A | 3/1995 | Boggs et al. ................ 430/343 |
| 5,534,393 A | 7/1996 | Boggs et al. ................ 430/348 |
| 5,667,943 A | 9/1997 | Boggs et al. ................ 430/343 |
| 6,054,246 A | 4/2000 | Bhatt et al. .................. 430/151 |
| 6,420,131 B1 | 7/2002 | Miller et al. .................. 435/25 |
| 6,537,410 B2 | 3/2003 | Arnost et al. ................ 156/235 |

FOREIGN PATENT DOCUMENTS

| GB | 1298462 | 12/1972 |
|---|---|---|
| JP | 62288828 A * | 12/1987 |
| JP | 04213368 | 8/1992 |

OTHER PUBLICATIONS

English language abstract of JP 62-288828.*
U.S. Appl. No. 10/789,648, filed Feb. 27, 2004, Chu et al.
U.S. Appl. No. 10/151,432, filed May 20, 2002, Bhatt et al.
Beilstein Institute for Organic Chemistry, Frankfurt-Main, Germany; (1988-2001); XP-002290704, pp. 1-4.
Beilstein Institute for Organic Chemistry, Frankfurt-Main, Germany; (1988-2001); XP-002290705, pp. 1-2.
Beilstein Institute for Organic Chemistry, Frankfurt-Main, Germany; (1988-2001); XP-002290706, pp. 1-2.
Beilstein Institute for Organic Chemistry, Frankfurt-Main, Germany; (1988-2001); XP-002290707, pp. 1-2.
Beilstein Institute for Organic Chemistry, Frankfurt-Main, Germany; (1988-2001); XP-002290708, pp. 1-2.

* cited by examiner

*Primary Examiner*—Amanda Walke
(74) *Attorney, Agent, or Firm*—Michel Morency; James F. Ewing; Foley & Lardner LLP

(57) ABSTRACT

There are described novel fluorescein dye compounds and imaging members and imaging methods utilizing the compounds. The fluorescein dye compounds exhibit a first color when in the crystalline form and a second color, different from the first color, when in the liquid, amorphous form.

17 Claims, No Drawings

DYES AND USE THEREOF IN THERMAL IMAGING MEMBERS AND METHODS

REFERENCE TO RELATED APPLICATIONS

This application claims the benefit of provisional application Ser. No. 60/451,208, filed Feb. 28, 2003.

This application is related to the following commonly assigned United States patent applications and patents, the disclosures of all of which are hereby incorporated by reference herein in their entirety:

U.S. patent application Ser. No. 10/789,648, filed on even date herewith;

U.S. Pat. No. 6,537,410 B2;

U.S. patent application Ser. No. 10/151,432 filed May 20, 2002 (U.S. Patent Application Publication No. US2003/0125206 A1) now U.S. Pat. No. 6,801,233 B2; and U.S. Pat. No. 6,054,246.

FIELD OF THE INVENTION

This invention relates to novel compounds and, more particularly, to compounds which exhibit one color in the crystalline form and a second, different color in the liquid, or amorphous, form. Also described are imaging members and methods, including thermal imaging members and methods, which utilize such dyes.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible. This would be the case for time-independent temperature of coloration.

Finally, the imaging system may comprise more than one color-forming layer and be designed to be printed with a single thermal print-head, as described in the above-mentioned patent application Ser. No. 10/151,432, now U.S. Pat. No. 6,801,233 B2. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204-5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274-275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

As the state of the imaging art advances and efforts are made to provide new imaging systems that can meet new performance requirements, and to reduce or eliminate some of the undesirable characteristics of the known systems, it would be advantageous to have new dye compounds which can be used in imaging systems including thermal imaging systems.

SUMMARY OF THE INVENTION

It is therefore an object of this invention to provide novel compounds.

Another object of the invention is to provide novel compounds which exhibit different colors when in the crystalline form and in the liquid form.

Yet another object of the invention is to provide imaging members and methods, including thermal imaging members and methods, which utilize the novel compounds.

The present invention provides novel fluorescein compounds that are useful as image dyes in imaging systems. According to one aspect of the invention there are provided novel fluorescein dye compounds which exhibit a first color when in the crystalline form and a second color, different from the first color, when in the liquid, amorphous form.

In one embodiment of the invention there are provided novel compounds which are represented by formula I

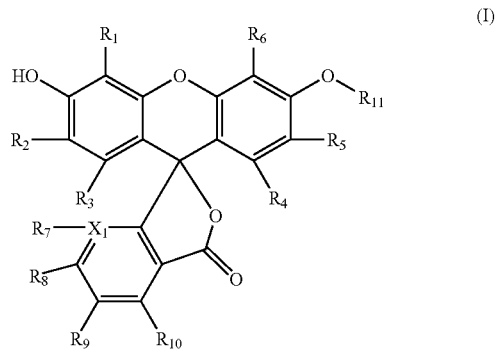

wherein:
$R_1$, $R_2$, $R_5$, $R_6$, $R_8$, $R_9$ and $R_{10}$ are each independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, substituted oxygen, substituted nitrogen, substituted sulfur, unsubstituted oxygen, unsubstituted nitrogen and unsubstituted sulfur;
$R_3$ and $R_4$ are each independently selected from the group consisting of hydrogen, alkyl having from 1 to 3 carbon atoms, substituted alkyl having from 1 to 3 carbon atoms, alkenyl having from 1 to 3 carbon atoms, substituted alkenyl having from 1 to 3 carbon atoms, alkynyl having from 1 to 3 carbon atoms, substituted alkynyl having from 1 to 3 carbon atoms, substituted oxygen, substituted nitrogen, and substituted sulfur;
$R_7$ is absent or selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, substituted oxygen, substituted nitrogen, substituted sulfur, unsubstituted oxygen, unsubstituted nitrogen and unsubstituted sulfur;

$R_{11}$ is selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, sulfonyl, aryl, substituted aryl, heteroaryl and substituted heteroaryl; and $X_1$ is carbon or nitrogen;

provided that at least one of $R_1$, $R_2$, $R_5$ and $R_6$ is selected from the group consisting of alkyl, preferably having from 1 to 18 carbon atoms, substituted alkyl, alkenyl, substituted alkenyl, alkynyl, substituted alkynyl, heterocycloalkyl, substituted heterocycloalkyl, aryl, substituted aryl, heteroaryl and substituted heteroaryl.

In a preferred group of compounds represented by formula I, X is carbon, $R_7$, $R_8$, $R_9$ and $R_{10}$ are each hydrogen and $R_1$, $R_2$, $R_3$, $R_4$, $R_5$, $R_6$ and $R_{11}$ are as previously defined.

Particularly preferred fluorescein compounds of the present invention are compounds of formula I in which $R_{11}$ is substituted or unsubstituted alkyl and two of $R_1$, $R_2$, $R_5$ and $R_6$ are substituted or unsubstituted alkyl, preferably having between one and twelve carbon atoms.

The conversion to the liquid form can be carried out by applying heat to the compounds and therefore the compounds are useful in thermal imaging members used in thermal imaging methods. In such thermal imaging methods thermal energy may be applied to the thermal imaging members by any of the techniques known in thermal imaging such as from a thermal print head, a laser, a heated stylus, etc. In another embodiment, the conversion to the liquid form may be effected by applying a solvent for the crystalline solid such as from an ink jet imaging apparatus to at least partially dissolve the crystalline material. In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to the liquid amorphous form to form the image.

The compounds of the invention may be incorporated in any suitable imaging members. Typical suitable imaging members generally comprise a substrate carrying at least one image-forming layer including a compound in the crystalline form, which can be converted, at least partially to a liquid in the amorphous form, the liquid having intrinsically a different color from the crystalline form. The imaging member may be monochrome or multicolor and the temperature at which an image is formed in at least one of the image-forming layers is preferably time independent. Preferred imaging members according to the invention are thermal imaging members.

Preferred thermal imaging members according to the invention are those having the structures described in prior co-pending commonly assigned U.S. patent application Ser. No. 09/745,700 filed Dec. 20, 2000, now U.S. Pat. No. 6,537,410 B1 which is hereby incorporated herein by reference in its entirety and made a part of this application.

Other preferred thermal imaging members are those having the structures described in prior, co-pending commonly assigned U.S. patent application Ser. No. 10/151,432 filed May 20, 2002, now U.S. Pat. No. 6,801,233 B2, which is hereby incorporated herein by reference in its entirety and made a part of this application.

Further preferred thermal imaging members are those having the structures described in U.S. Pat. No. 6,054,246 which is hereby incorporated herein by reference in its entirety and made a part of this application.

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric forms, only one of such isomeric forms is commonly present in the crystalline state. In amorphous form or solution, on the other hand, the compound may explore its whole conformational and isomeric space, and only a small proportion of the population of individual molecules of the compound may at any one time exhibit the particular conformation or isomeric form adopted in the crystal. Compounds of the present invention exhibit tautomerism in which at least one tautomeric form is colorless, and at least another tautomeric form is colored. The crystalline form of compounds of the present invention comprises predominantly the colorless tautomer.

A first embodiment of the invention is a compound whose colorless tautomer is represented by formula I as described above.

Representative compounds according to the invention are those of formula I in which $R_3$, $R_4$, $R_8$, $R_9$ and $R_{10}$ are each hydrogen, and the other substituents are as shown in Table I:

TABLE I

| Dye | R1 | R2 | R5 | R6 | R7 | R11 | X1 |
|---|---|---|---|---|---|---|---|
| I | H | $C_6H_{13}$ | $C_6H_{13}$ | H | H | $CH_2C_6H_5$ | C |
| II | H | $C_6H_{13}$ | $C_6H_{13}$ | H | — | $CH_2CH_3$ | N |
| III | H | $CH_2CH_3$ | $CH_2CH_3$ | H | H | $CH_2C_6H_5$ | C |
| IV | H | $C_6H_{13}$ | $C_6H_{13}$ | H | H | $CH_2CH_3$ | C |
| V | $CH_3$ | H | H | $CH_3$ | H | $CH_2C_6H_5$ | C |
| VI | $CH_3$ | H | H | $CH_3$ | H | $CH_2CH_2OCH_3$ | C |
| VII | H | $CH_2CH_3$ | $CH_2CH_3$ | H | H | $CH_2CH_2CH(CH_3)_2$ | C |
| VIII | H | $CH_2CH_3$ | $CH_2CH_3$ | H | H | $CH_2(2\text{-}CH_3\text{—}C_6H_4)$ | C |
| IX | H | $CH_2CH_3$ | $CH_2CH_3$ | H | H | $CH_2(3\text{-}CH_3\text{—}C_6H_4)$ | C |
| X | H | $CH_2C_6H_5$ | $CH_2C_6H_5$ | H | H | $CH_2C_6H_5$ | C |
| XI | H | $C_3H_7$ | $C_3H_7$ | H | H | $CH_2C_6H_5$ | C |
| XII | H | $CH_2C_6H_5$ | $CH_2C_6H_5$ | H | H | $CH_2CH_2CH(CH_3)_2$ | C |
| XIII | H | $CH_2CH_3$ | $CH_2CH_3$ | H | H | $CH_2(4\text{-}CH_3\text{—}C_6H_4)$ | C |

TABLE I-continued

| Dye | R1 | R2 | R5 | R6 | R7 | R11 | X1 |
|---|---|---|---|---|---|---|---|
| XIV | H | $CH_2CH_3$ | $CH_2CH_3$ | H | H | $CH_2(3\text{-}Cl\text{—}C_6H_4)$ | C |
| XV | H | $CH_2CH_3$ | $CH_2CH_3$ | H | H | $CH_2(4\text{-}Cl\text{—}C_6H_4)$ | C |

Definitions

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylamino and dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

According to the invention, there have been provided molecules exhibiting tautomerism in which at least one tautomeric form is colorless, and at least another tautomeric form is colored. Crystallization of the equilibrating mixture of the two tautomeric forms is carried out so as to produce colorless crystals. The solvent chosen to perform the crystallization will typically be one of such polarity (and other chemical properties, such as hydrogen-bonding ability) that the pure colorless crystal form is favored, either in the equilibrium between the colorless and colored forms in solution, or in having lower solubility in the solvent than the colored form. The choice of solvent is usually determined empirically for a particular mixture of tautomers.

Upon conversion of the pure crystalline colorless form, the equilibrium between the two tautomers is re-established in the resulting amorphous (liquid) phase. The proportion of the amorphous material that is colored (i.e., the proportion that is in the colored tautomeric form) may vary, but is preferably at least about 10%.

The colored and colorless tautomeric forms of the molecules of the present invention must meet certain criteria for image quality and permanence. The colorless form, which is preferably the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.).

The compounds of the invention may be prepared by synthetic processes which are known to those skilled in the art, particularly in view of the state of the art and the specific preparatory examples provided below herein.

Generally, the novel fluorescein ethers of this invention can be synthesized in three steps when starting with a substituted resorcinol or five steps when the substituted resorcinol is not commercially available. Commercially available substituted resorcinols are 4-ethylresorcinol, 4-hexylresorcinol, 4-benzylresorcinol and 2-methyl resorcinol. 3-Propylresorcinol can be prepared from the commercially available 2,4-dihydroxypropiophenone by reduction with alkaline sodium borohydride as described in Agricultural and Biological Chemistry, 53, 3087 (1989).

The substituted resorcinols can be converted to fluoresceins by heating two equivalents of resorcinol with one equivalent of cyclic anhydride in a strong acid such as sulfuric acid as described in Zh. Obshch.Khim. 18, 1801 (1948), or methane sulfonic acid as described in Journal of Organic Chemistry 62, 6469 (1997). Phthalic anhydrides are preferred but aliphatic anhydrides can also be used.

The fluoresceins can be alkylated with reactive alkylating agents using the method described in Can. J. Chem 63, 1320 (1985) and U.S. Pat. No. 6,420,131. The fluorescein predominantly alkylates twice to give the monoether ester, but the diether is a common impurity. Hydrolysis with aqueous lithium or sodium hydroxide followed by purification to remove any diether provides the compounds of the invention as yellow solids.

Careful recrystallization from solvent mixtures such as hexanes/acetone or hexanes/ethyl acetate produces white crystalline material which is preferred for use in thermal imaging members.

The thermal imaging members of the invention can be direct thermal imaging members wherein an image is formed in the member itself or they can be thermal transfer imaging members whereby image-forming material is transferred to an image-receiving member. The melting point of the molecules used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize with a conventional thermal print head. It should be noted, however, that there are uses for certain novel compounds of the present invention that do not require the use of thermal print heads (for example, laser imaging).

To form a preferred direct thermal imaging system, the crystalline, colorless form of the compounds of the invention is made into a dispersion in a solvent in which the compound is insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitrites, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrollidone) and cellulose derivatives, water-dispersed latices such as styrene/butadiene or poly(urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Mayer rod, roll, cascade, spray, and curtain coating techniques. The image-forming layer so formed is optionally overcoated with a protective layer or layers.

Where materials of the present invention are used to prepare an imaging medium of the type described in copending U.S. patent application Ser. No. 10/151,432 filed May 20, 2002, now U.S. Pat. No. 6,801,233 B2, the process described above is followed for each of the imaging layers. Successive layers may be coated sequentially, in tandem, or in a combination of sequential and tandem coatings.

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example I

Synthesis of Dye I

Step 1a. Synthesis of 2,7-dihexylfluorescein

To phthalic anhydride (38.12 g, 257.4 mmol, 1 eq) there was added 4-hexylresorcinol (100 g, 514.7 mmol, 2 eq) followed by the addition of methane sulfonic acid (400 mL). The reaction mixture was stirred at 100-105° C. for 45 minutes, cooled to room temperature, poured into water (5 L), stirred for one hour, filtered and the filter cake was washed with of water (1.7 L). The product was dried in a vacuum oven for 16 hours at 70° C. until dry and then suspended in acetone (650 mL), stirred overnight, filtered and dried in a vacuum oven at 50° C. for 2 hours to yield of a yellow powder (115 g). The crude product was re-suspended in acetone (1150 mL), stirred for three hours, filtered and dried in a vacuum oven to give a yellow powder (110 g, 220 mmol, 85.5% yield).

Step 1b. Alkylation of 2,7-dihexylfluorescein 2,7-Dihexylfluorescein (5.0 g, 10 mmol, 1 eq) and potassium carbonate (30 mmol, 3 eq) were added to dimethylformamide (50 mL), at room temperature and the mixture was stirred with heating at 100° C. until the reddish solution appeared clear. Benzyl bromide (4.3 g, 25 mmol, 2.5 eq) dissolved in dimethlyformamide (10 mL) was slowly added to the anionic fluorescein solution over approximately 10 minutes and the mixture was further stirred at 100° C. for 6 hours. After cooling the reaction mixture was poured into water (600 mL) and the pH adjusted to 3. The precipitated product, the monoether ester, was filtered and hydrolyzed without further purification.

Step 1c. Synthesis of Dye I.

The monoether ester product of Step 1b was dissolved in a mixture of acetone (60 mL), water (20 mL) and aqueous sodium hydroxide (16 mL, 40 mmol, 4 eq, 10% NaOH. The mixture was stirred at room temperature for 16 hours. The reaction was followed by TLC (5% methanol in methylene chloride). After evaporation of acetone the mixture was diluted with water (300 mL) and filtered to remove water-insoluble material. The filtrate was neutralized with dilute hydrochloric acid to give a pale yellow precipitate.

The crude product was purified by column chromatography (3% methanol in methylene chloride) followed by recrystallization from a mixture of hexane and acetone to give the desired product as colorless crystals, m.p. 111-113° C. (3.0 g, 5.1 mmol, 51% yield).

The structure was confirmed by NMR and mass spectroscopy.

Example II

Synthesis of Dye II

Step 2a. Synthesis of 2,7-dihexylazafluorescein

Concentrated sulfuric acid (ca. 25 drops) was added to a mixture of 4-hexylresorcinol (5.0 g, 25.7 mmol) and 3-azaphthalic anhydride (1.9 g, 12.7 mmol) at room temperature and the mixture was then stirred with heating at 160° C. for 5 hours. After cooling, the mixture was dissolved in 10% sodium hydroxide and neutralized with hydrochloric acid to give a precipitate. The crude product was purified by column chromatography (eluent; 10% methanol in methylene chloride) to give the desired product (4.0 g, 8.0 mmol, 63% yield).

Step 2b. Alkylation of 2,7-dihexylazafluorescein 2,7-Dihexylazafluorescein (3.5 g, 7.0 mmol) and potassium carbonate (17.5 mmol 2.5 eq) were dispersed in dimethylformamide (30 mL) at room temperature and the mixture was then stirred with heating at 90° C. until a reddish clear solution appeared. To the anionic fluorescein solution, a solution of ethyl tosylate (6.0 g, 27.9 mmol, 4 eq), in dimethylformamide (10 mL), was added slowly over 10 minutes followed by further stirring at 100° C. for another 2 hours. After cooling, the mixture was poured into water (500 mL) and the precipitated product, the monoether ester, was filtered and hydrolyzed without further purification.

Step 2c. Synthesis of Dye II

The monoether ester product from Step 2c was dissolved in ethanol (40 mL) and 10% aqueous sodium hydroxide (11 mL, 28 mmol, 4 eq) was added to the solution. The mixture was stirred at room temperature for 3 hours. After evaporation of ethanol the mixture was diluted with water (300 mL) and filtered. The filtrate was neutralized with dilute hydrochloric acid to give a pale yellow precipitate. The crude product was purified by column chromatography (5% methanol in methylene chloride) followed by recrystallization from hexane to give the desired product as colorless crystals (m.p. 158-160° C.).

The structure was confirmed by NMR and mass spectroscopy

Example III

Synthesis of Dye III

Step 3a. Synthesis of 2'7'-diethylfluorescein

Phthalic anhydride (3.81 g, 25.7 mmol, 1 eq) and 4-ethylresorcinol (7.1 g, 51.4 mmol, 2 eq) were stirred in 73% sulfuric acid (15 mL) at 160° C. for 5 hours. The reaction mixture was cooled, diluted with water (50 mL) and filtered. The product was suspended in water (50 mL) and filtered. This operation was repeated four times. The product was dried in a vacuum oven at 85° C. for 5 hours to give the desired product, m.p. 271-273° C. (9.2 g, 24.4 mmol, 95% yield).

Step 3b. Benzylation of 2,7-diethylfluorescein.

Benzyl bromide (7.9 ml, 66.5 mmol, 2.5 eq was added to a mixture of 2,7-diethylfluorescein (10 g, 26.6 mmol, 1 eq) and potassium carbonate (12.85 g, 93.1 mmol, 3.5 eq) in dimethylformamide (120 ml). The reaction mixture was heated to 80° C. and stirred for 26 hours. The reaction mixture was cooled and poured into water (1400 mL), the pH brought to 3.0 and the yellow precipitate was filtered off. This product was used in the next step without purification.

Step 3c. Synthesis of Dye III

Water (100 mL) and lithium hydroxide (5.58 g, 133 mmol, 5 eq) were added to a solution of 2,7-diethylfluorescein benzyl ether benzyl ester (the product from Step 3b) in tetrahydrofuran (200 ml) The reaction mixture was stirred under a blanket of nitrogen at room temperature for 60 hours. The pH was brought to 3.5-4.0 and two layers formed. The layers were separated and the aqueous layer was washed with ethyl acetate (2×75 mL). The organic layers were combined, dried over $MgSO_4$, filtered and evaporated to dryness. The residue was dissolved in hot acetone and hexane was added until crystallization started. The product was filtered and dried to give 2.41 g of the desired product, m.p. 222° C. The filtrate was evaporated to dryness to give 4.74 g of impure material. The overall yield was 7.15 g (56.4%).

The structure was confirmed by NMR and mass spectroscopy.

Example IV

Synthesis of Dye IV

Step 4a. Alkylation of 2',7'-hexylfluorescein

To 2,7-dihexylfluorescein (50 g, 100 mmol, 1 eq) in dimethylformamide (354 mL), there was added ethyl p-toluenesulfonate (60.08 g, 300 mmol, 3 eq) and potassium carbonate (80 g, 580 mmol, 5.8 eq). The reaction mixture was stirred at 80° C. for 6.5 hours (the reaction mixture was very viscous). The reaction mixture was cooled to room temperature and poured into water (3 L). The pH was adjusted to 3.0 and mixture was stirred for 1.5 hours. The precipitated product was filtered and used in the next step without purification.

Step 4b. Synthesis of Dye IV.

Lithium hydroxide hydrate (20.98 g, 500 mmol, 5 eq) was added to a solution of the mono ethyl ether, ethyl ester of 2,7-dihexylfluorescein (55.6 g, 100 mmol, 1 eq) in a mixture of tetrahydrofuran (764 mL) and water (367 mL), and reaction mixture was stirred at 60° C. overnight. The reaction mixture was cooled to room temperature and the pH adjusted to 4.0. The organic layer was separated and the aqueous layer was washed with ethyl acetate (300 ml). The organic layers were combined, washed with water, dried over magnesium sulfate and concentrated to dryness to give 45.2 g of crude product (85 mmol, 85% yield). The crude product was purified by column chromatography (Silica gel, 5% MeOH in dichloromethane). The purified product was crystallized from hexane/acetone (25:1), and pale yellow crystals were collected and washed with the same solvent. The product was suspended again in 115 mL of 5% acetone in hexane, stirred overnight at ambient temperature, filtered, washed with 2.5% acetone in hexane and dried. This process was repeated until the dried desired product was nearly white, m.p. 105-107° C. (10.5 g, 19.7 mmol, 20% yield).

The structure was confirmed by NMR and mass spectroscopy.

Example V

Synthesis of Dye V

Step 5a. Synthesis of 4,5-dimethylfluorescein

To a mixture of 2-methylresorcinol (10.0 g; 80.6 mmol) and phthalic anhydride (40.3 mmol; 6.0 g) there was added 73% (w/w) sulfuric acid (24 mL) at room temperature and the mixture was then stirred with heating at 160° C. for 3 hours. After cooling the mixture was poured into water (300 mL) with stirring. The precipitated product was filtered and washed with water several times to give a yellow product in quantitative yield. The structure was confirmed by NMR and mass spectroscopy.

Step 5b. Alkylation of 4,5-dimethylfluorescein 4,5-Dimethylfluorescein (5 g; 13.9 mmol) and potassium carbonate (69.5 mmol, 5 eq) were dispersed in dimethylformamide (50 mL) at room temperature. The mixture was then stirred with heating at 100° C. until a reddish clear solution appeared. Benzyl bromide (7.1 g, 41.7 mmol; 3 eq) dissolved in dimethylformamide (10 mL) was added to the solution slowly over 10 minutes. Followed by stirring the mixture at 100° C. for another 3 hours. After cooling the mixture was poured into water (700 mL) and the pH was adjusted to 3. The precipitated product, the monoether ester, was filtered and hydrolyzed without further purification.

Step 5c. Synthesis of Dye V

The monoether ester product from Step 5b was dissolved in a mixture of acetone (70 mL) and water (13 mL) and 10% aqueous sodium hydroxide (23 mL, 55.6 mmol, 4 eq) was added. The mixture was stirred at room temperature overnight. After the evaporation of acetone the mixture was diluted with water (500 mL), and filtered. The filtrate was neutralized with dilute hydrochloric acid to give a pale yellow precipitate. The crude product was purified by column chromatography (eluent; 3% methanol in methylene chloride) followed by recrystallization from a mixture of hexane and acetone to give the desired product as colorless crystals (m.p. 220-222° C.).

The structure was confirmed by NMR and Mass spectroscopy.

Example VI

Synthesis of Dye VI

Step 6a. Alkylation of 4,5-dimethylfluorescein 4,5-Dimethylfluorescein (5 g; 13.9 mmol) and potassium carbonate (69.5 mmol, 5 eq) were dispersed in dimethylformamide (50 mL) at room temperature and the mixture was stirred with heating at 100° C. until a reddish clear solution appeared. A solution of methoxyethyl tosylate (12.8 g, 55.6 mmol, 4 eq) in dimethylformamide (10 mL) was added to the anionic fluorescein solution slowly over 10 minutes followed by further stirring at 100° C. for another 3 hours. After cooling to room temperature the mixture was poured into water (700 mL) and the pH was adjusted to 3. The precipitated crude product, the monoether ester, was filtered and hydrolyzed without further purification.

Step 6b. Synthesis of Dye VI

The monoether ester product was dissolved in a mixture of acetone (70 mL) and water (13 mL) and 10% aqueous sodium hydroxide were added (23 mL, 55.6 mmol, 4 eq). The reaction mixture was stirred at room temperature overnight. After the evaporation of acetone the mixture was diluted with water (500 mL) and filtered. The filtrate was neutralized with dilute hydrochloric acid to give a pale yellow precipitate. The crude product was purified by column chromatography (5% methanol in methylene chloride) followed by recrystallization from a mixture of hexane and acetone to give the desired product as colorless crystals, m.p. 245-247° C. (4.0 g, 9.66 mmol, 69.5% yield).

The structure was confirmed by NMR and mass spectroscopy.

Example VII

Synthesis of Dye VII

Step 7a. Alkylation of 2,7-diethylfluorescein 2,7-Diethylfluorescein (3 g; 7.7 mmol) and potassium carbonate (30.9 mmol, 4 eq) were dispersed in dimethylformamide (30 mL) at room temperature and the mixture was stirred with heating at 100° C. until a reddish clear solution appeared. A solution of benzyl bromide (7.1 g, 41.7 mmol, 3 eq) in dimethylformamide (5 mL) was added to the anionic fluorescein solution, slowly over 10 minutes followed by stirring the mixture at 100° C. for another 3 hours. After cooling, the mixture was poured into water (300 mL) and the pH was adjusted to 3. The precipitated crude product, the monoether ester, was filtered and hydrolyzed without further purification.

Step 7b. Synthesis of Dye VII

The monoether ester product was dissolved in a mixture of acetone (70 mL) and water (20 mL) and 10% aqueous sodium hydroxide (13 mL, 30.9 mmol, 4 eq) was added. The mixture was stirred at room temperature overnight. After the evaporation of acetone the mixture was diluted with water (500 mL) and filtered. The filtrate was neutralized with dilute hydrochloric acid to give a pale yellow precipitate. The crude product was purified by column chromatography (5% methanol in methylene chloride) followed by recrystallization from a mixture of hexane and acetone to give 1.9 g of the desired product as colorless crystals; m.p.185-187° C. (1.9 g, 4.16 mmol, 54% yield).

The structure was confirmed by NMR and mass spectroscopy.

Example VIII

Synthesis of Dye VIII

Step 8a. Alkylation of 2',7'-diethylfluorescein

To a mixture of 2',7'-diethylfluorescein (5 g, 13.30 mmol, 1 eq) and potassium carbonate (6.42 g, 46.55 mmol, 3.5 eq) in dimethylformamide (50 ml) there was added 2-methylbenzyl bromide (6.15 g, 33.24 mmol, 2.5 eq). The reaction mixture was stirred at 85° C. for 14 hours. The reaction mixture was cooled and poured into water (650 mL), the pH brought to 3.0 and an orange precipitate was filtered off. This material was used in the next step without purification.

Step 8b. Synthesis of Dye VIII

Lithium hydroxide (2.79 g, 66.5 mmol, 5 eq) and water (51 mL) were added to a solution of the 2',7'-diethylfluorescein 2-methylbenzyl ether 2-methylbenzyl ester in tetrahydrofuran (102 mL). The reaction mixture was stirred under a blanket of nitrogen at room temperature for 20 hours and then at 60° C. for 3 hours. The reaction mixture was cooled, the pH brought to 4.0 and two layers were formed. The layers were separated and the aqueous layer was washed with ethyl acetate (2×50 mL). The combined organic layers were dried over MgSO$_4$, filtered and evaporated to dryness. The residue was crystallized from toluene/hexanes. The crystalline product was filtered and dried in a vacuum oven to give 2.2 g of dark yellow material. Part of this material was crystallized from methanol and dried to give the desired product as yellow crystals, m.p. 184° C. (2.2 g, 4.66 mmol, 34% yield).

The structure was confirmed by NMR and mass spectroscopy.

Example IX

Synthesis of Dye IX

Step 9a. Alkylation of 2',7'-diethylfluorescein

3-Methylbenzyl bromide (6.15 g, 33.24 mmol, 2.5 eq) was added to a mixture of 2,7-diethylfluorescein (5 g, 13.30 mmol, 1 eq) and potassium carbonate (6.42 g, 46.55 mmol, 3.5 eq) in dimethylformamide (50 mL). The reaction mixture was stirred at 85° C. for 16 hours. The reaction mixture was cooled and poured into water (650 mL), the pH brought to 3.0 and an orange precipitate was filtered off. This material was used in the next step without purification.

Step 9b. Synthesis of Dye IX

Lithium hydroxide (2.79 g, 66.5 mmol, 5 eq) and water (51 mL) were added to a solution of 2,7-diethylfluorescein 3-methylbenzyl ether 3-methylbenzyl ester in tetrahydrofuran (102 mL). The reaction mixture was stirred under a blanket of nitrogen at room temperature for 20 hours and then at 65° C. for 4 hours. The reaction mixture was cooled, the pH brought to 4.0 and two layers were formed. The layers were separated and the aqueous layer was washed with ethyl acetate (2×50 mL). The combined organic layers were dried over magnesium sulfate, filtered and evaporated to dryness. The residue was crystallized from toluene/hexanes to give a dark yellow material (3.1 g, 6.3 mmol, 47% yield). Part of this material was recrystallized from methanol to give the desired product as yellow crystals, m.p. 158-162° C.

The structure was confirmed by NMR and mass spectroscopy.

Example X

Synthesis of Dye X

Step 10a. Synthesis of 2',7'-dibenzylfluorescein

Phthalic anhydride (7.5 gm, 0.05 mol) was reacted with 4-benzylresorcinol (22 gm, 0.11 mol) in methanesulfonic acid (35 mL) at 95-103° C. for two hours and isolated as described in the previous examples. Purification by stirring with acetone (400 mL), filtering, washing with acetone and drying provided the fluorescein as a yellow solid (30 gm, 73% yield).

Step 10b. Alkylation of 2,7-dibenzylfluorescein

2',7'-Dibenzylfluorescein (3 g, 5.9 mmol) and potassium carbonate (23.4 mmol, 4 eq) were dispersed in dimethylformamide (35 mL) at room temperature and the mixture was stirred with heating at 100° C. until a reddish clear solution appeared. A solution of benzyl bromide (4.0 g, 23.4 mmol, 4 eq) dissolved in dimethylformamide (5 mL) was added slowly to the anionic fluorescein solution over 10 minutes followed by stirring at 100° C. for 3 hours. After cooling the mixture was poured into water (500 mL) and the pH was adjusted to 3. The precipitated crude product, the monoether ester, was filtered and was hydrolyzed without further purification.

Step 10c. Synthesis of Dye X

The monoether ester product was dissolved in a mixture of acetone (70 mL) and water (25 mL) and 10% aqueous sodium hydroxide was added (9 mL, 23.4 mmol, 4 eq). The mixture was stirred at room temperature overnight. After the evaporation of acetone the mixture was diluted with water (500 mL) and filtered. The filtrate was neutralized with dilute hydrochloric acid to give a pale yellow precipitate. The crude product was purified by column chromatography (5% methanol in methylene chloride) followed by recrystallization from a mixture of hexane and acetone to give the desired product as colorless crystals, m.p. 210-212° C.

The structure was confirmed by NMR and mass spectroscopy.

Example XI

Synthesis of Dye XI

Step 11a. Synthesis of 4-propylresorcinol

A 12 L round bottom flask equipped with a mechanical stirrer, reflux condenser and nitrogen inlet was charged with of sodium hydroxide (440 g, 11 moles) and 4.5 L of distilled water. Sodium borohydride (440 g, 11.6 moles) was added and the batch was held at 50° C. until all the solids dissolved. To the mixture there was added 2,4-dihydroxypropiophenone (440 g, 2.6 moles) resulting in a 10-15° C. exotherm and some hydrogen evolution. The batch was held at 80° C. for 90 minutes then cooled to 10-20° C. in an ice bath. Hydrogen evolution was observed during the 90 minute hold at 80° C. 1.9 kg of hydrochloric acid (37%) was added drop-wise (hydrogen evolution) bringing the batch to pH 6. The product was extracted into methylene chloride (5×500 mL). The methylene chloride was stripped off and replaced with toluene (2 L). The product was crystallized from toluene to give propyl resorcinol (261.5 g, 1.7 mol, 65% yield).

Step 11b. Synthesis of 2'7'-dipropylfluorescein

A 3 L round bottom flask equipped with a mechanical stirrer and nitrogen inlet was charged with propylresorcinol (557 g, 3.66 mol) and phthalic anhydride (271 g, 1.83 mol) in methanesulfonic acid (1.4 L). The mixture was held at 90° C. for 1 hour. The batch was then cooled to 50° C. and slowly quenched into 10 L ice water. The product was filtered off, washed with water (3×1 L) and dried to yield 885 g of crude product. The crude product was suspended in 2.6 L acetone and heated to reflux. The product was filtered, washed with acetone and vacuum dried to give the product as a yellow solid (665 g, 1.57 mol, 86% yield, 90 wt % by HPLC).

Step 11c. Alkylation of 2',7'-dipropylfluorescein

A 1 L round bottom flask equipped with a mechanical stirrer and nitrogen inlet was charged with dipropylfluorescein (144 g, 0.35 mol) and sodium carbonate (217 g, 2 mol) in dimethylformamide (600 mL). The batch was held at 80° C. while benzyl bromide (146 g, 0.853 mol) was added drop-wise over 1 hour. The batch was held at 80° C. for 4 hours (TLC: 5% methanol:methylenechloride) then distilled water (200 mL) was added and the batch was cooled to 25° C. The product was filtered, washed with 3:1 dimethylformamide:water, (100 mL) then water (3×ϕmL) to give dry product (155 g, 0.26 mol, 75% yield).

The structure was confirmed by NMR and mass spectroscopy.

Step 11d. Synthesis of Dye XI:

A 2 L round bottom flask equipped with a mechanical stirrer, reflux condenser and nitrogen inlet was charged with fluorescein benzylester (155 g, 0.26 mol) in acetone (1 L) and 10% sodium hydroxide (126 mL). The batch was held at 60° C. for 4 hours (TLC 1:1 ethyl acetate:hexane, silica). The batch was quenched slowly into 5% hydrochloric acid (4 L). The solid was filtered off, washed with water and dried to give a yellow solid (140 g). The crude dye was suspended in ethyl acetate (400 mL) and held at reflux for 2 hours. The reaction mixture was cooled to 25° C., filtered, washed with ethyl acetate (50 mL) and then with hexane (3×100 mL)to give a dry white solid, m.p. 202-203° C. (99 g, 0.19 mol, 75% yield).

The structure was confirmed by NMR and mass spectroscopy.

Example XII

Synthesis of Dye XII

Step 12a. Alkylation of 2',7'-dibenzylfluorescein

2',7-Dibenzylfluorescein (17.4 g, 0.034 mol) and sodium carbonate (18 g, 0.17 mol) were dissolved in dimethylformamide (80 mL) and heated to 70° C. After 15 minutes, 3-methyl-1-butylbromide (15.1 g, 0.10 mol) was added dropwise over 15 minutes. The reaction mixture was heated for 5 hours at 80° C. TLC showed a complete reaction and product began to crystallize from the reaction mixture. Water (20 mL) was added slowly dropwise and the mixture was allowed to cool slowly to room temperature. The solid was collected by suction filtration, washed well with water and air-dried to yield an orange powder (18 g, 0.027 mmol, 81% yield) which was directly used in the next step.

Step 12b. Synthesis of Dye XII

The ester (16.6 g, 0.025 mol) from Step 12a was dissolved in acetone (150 mL) and heated to gentle reflux. Lithium hydroxide (20%, 20 mL) was added and the reaction was heated at 60° C. for 18 hours. The reaction mixture was slowly added to water (400 mL) and acidified to pH 3 with concentrated hydrochloric acid. The product was filtered, washed with water to afford the desired product (14.2 g, 0.024 mol, 97% yield). Recrystallization from chlorobenzene produced white, crystalline material, m.p. 199-201° C.

The structure was confirmed by NMR and mass spectroscopy.

Example XIII

Synthesis of Dye XIII

Step 13a. Alkylation of 2',7'-diethylfluorescein

To a mixture of 2',7'-diethylfluorescein (4 g, 10.64 mmol, 1 eq) and potassium carbonate (5.14 g, 37.24 mmol, 3.5 eq) in dimethylformamide (50 mL) was added 4-methylbenzyl bromide (4.29 g, 26.60 mmol, 2.5 eq). The reaction mixture was stirred at 95° C. for 24 hours and then at 105° C. for 20 hours. The reaction mixture was cooled and poured into water (700 mL), the pH brought to 4.5-5.0 and an orange precipitate was filtered off. This material was used in the next step without purification.

Step 13b. Synthesis of Dye XIII

To a solution of 2',7'-diethylfluorescein 4-methylbenzyl ether 4-methylbenzyl ester (the product from Step 13a) in tetrahydrofuran (82 mL) was added lithium hydroxide (2.23 g, 53.2 mmol, 5 eq) and water (41 mL). The reaction mixture was stirred under a blanket of nitrogen at room temperature for 20 hours and then at 70° C. for 4 hours. The reaction mixture was cooled, the pH brought to 4.0 and two layers were formed. The layers were separated and the aqueous layer was washed with ethyl acetate (2×50 mL). The organic layers were combined and dried over magnesium sulfate, filtered and evaporated to dryness. The residue recrystallized from toluene/hexane to give 2.2 g of dark yellow material. Part of this material was recrystallized from methanol to give the desired product as yellow crystals, m.p. 219-221° C. (2.2 g, 4.5 mmol, 42% yield).

The structure was confirmed by NMR and mass spectroscopy.

Example XIV

Synthesis of Dye XIV

Step 14a. Alkylation of 2',7'-diethylfluorescein

To a mixture of 2,7-diethylfluorescein (5 g, 13.30 mmol, 1 eq) and potassium carbonate (6.42 g, 46.55 mmol, 3.5 eq) in dimethylformamide (60 mL) was added 3-chlorobenzyl bromide (6.83 g, 33.25 mmol, 2.5 eq). The reaction mixture was stirred at 110° C. for 24 hours. The reaction mixture was cooled and poured into water (700 mL). The pH was brought to 3.0 and the precipitate was filtered off. This material was used in the next step without purification.

Step 14b. Synthesis of Dye XIV

To the solution of 2',7'-diethylfluorescein 3-chlorobenzyl ether 3-chlorobenzyl ester (product from Step 14b) in tetrahydrofuran (102 mL) was added lithium hydroxide (2.79 g, 66.5 mmol, 5 eq) and water (51 mL). The reaction mixture was stirred under a blanket of nitrogen at room temperature for 20 hours. The pH was brought to 4.0 and two layers were formed. The layers were separated and the aqueous layer was washed with ethyl acetate (2×60 mL). The organic layers were combined and dried over magnesium sulfate, filtered and evaporated to dryness. The residue was recrystallized from toluene/hexane to give the desired product as a pale yellow solid, m.p. 173-175° C. (2.3 g, 4.5 mmol, 34% yield).

The structure was confirmed by NMR and mass spectroscopy.

Example XV

Synthesis of Dye XV

Step 15a. Alkylation of 2',7'-diethylfluorescein

To a mixture of 2',7'-diethylfluorescein (5 g, 13.30 mmol, 1 eq) and potassium carbonate (6.42 g, 46.55 mmol, 3.5 eq) in dimethylformamide (60 mL) was added 4-chlorobenzyl bromide (6.83 g, 33.25 mmol, 2.5 eq. The reaction mixture was stirred at 110° C. for 24 hours. The reaction mixture was cooled and poured into water (700 mL). The pH was brought to 3.0 and the precipitate was filtered off. This material was used in the next step without purification.

Step 15b. Synthesis of Dye XV

To a solution of 2',7'-diethylfluorescein 4-chlorobenzyl ether 4-chlorobenzyl ester (product from Step 15a) in tetrahydrofuran (102 mL) was added lithium hydroxide (2.79 g, 66.5 mmol, 5 eq) and water (51 mL). The reaction mixture was stirred under a blanket of nitrogen at room temperature for 22 hours. The pH was brought to 4.0 and two layers were formed. The layers were separated and the aqueous layer was washed with ethyl acetate (2×60 mL). The combined organic layers were dried over magnesium sulfate, filtered and evaporated to dryness. The residue was recrystallized from acetone/hexane and dried to give the desired product, m.p. 188-191° C. (1.2 g, 2.34 mmol, 17% yield).

Although the invention has been described in detail with respect to various preferred embodiments, it is not intended to be limited thereto, but rather those skilled in the art will recognize that variations and modifications are possible which are within the spirit of the invention and the scope of the appended claims.

What is claimed is:

1. A compound represented by the formula wherein:

$R_1$, $R_2$, $R_5$, $R_6$, $R_8$, $R_9$ and $R_{10}$ are each independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_3$ and $R_4$ are each independently selected from the group consisting of hydrogen, alkyl having from 1 to 3 carbon atoms, substituted alkyl having from 1 to 3 carbon atoms, alkenyl having from 1 to 3 carbon atoms, substituted alkenyl having from 1 to 3 carbon atoms, alkynyl having from 1 to 3 carbon atoms, substituted alkynyl having from 1 to 3 carbon atoms, substituted oxygen, substituted nitrogen, and substituted sulfur;

$R_7$ is absent or selected from the group consisting of hydrogen, alkyl, substituted alkyl, alkenyl, substituted alkenyl, alkynyl, substituted alkynyl, heterocycloalkyl substituted heterocycloalkyl substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_{11}$ is selected from the group consisting of alkyl, substituted alkyl, alkenyl, substituted alkenyl, alkynyl, substituted alkynyl, heterocycloalkyl, substituted heterocycloalkyl, substituted carbonyl, acylamino, sulfonyl, aryl, substituted aryl, heteroaryl and substituted heteroaryl; and $X_1$ is carbon or nitrogen;

provided that at least one of $R_1$, $R_2$, $R_5$ and $R_6$ is selected from the group consisting of alkyl, substituted alkyl, alkenyl, substituted alkenyl, alkynyl, substituted alkynyl, heterocycloalkyl, substituted heterocycloalkyl, aryl, substituted aryl, heteroaryl and substituted heteroaryl.

2. A compound according to claim 1 wherein $X_1$ is carbon, $R_7$, $R_8$, $R_9$ and $R_{10}$ are each hydrogen and $R_1$, $R_2$, $R_3$, $R_4$, $R_5$, $R_6$ and $R_{11}$ are as defined in claim 1.

3. A compound according to claim 1 wherein $R_{11}$ is alkyl or substituted alkyl and two of $R_1$, $R_2$, $R_5$ and $R_6$ are alkyl or substituted alkyl having between one and twelve carbon atoms and $X_1$ is carbon.

4. A compound according to claim 1 wherein $R_1$, $R_3$, $R_4$, $R_6$, $R_7$, $R_8$, $R_9$ and $R_{10}$ are each hydrogen, $R_2$ and $R_5$ are each alkyl having 6 carbon atoms, $R_{11}$ is ethyl and $X_1$ is carbon.

5. A compound according to claim 1 wherein $R_1$, $R_3$, $R_4$, $R_6$, $R_7$, $R_8$, $R_9$ and $R_{10}$ are each hydrogen, $R_2$ and $R_5$ are each alkyl having 3 carbon atoms, $R_{11}$ is benzyl and X is carbon.

6. A compound according to claim 1 wherein $R_1$, $R_3$, $R_4$, $R_6$, $R_7$, $R_8$, $R_9$ and $R_{10}$ are each hydrogen, $R_2$ and $R_5$ are each benzyl, $R_{11}$ is —$CH_2CH_2CH(CH_3)_2$, and $X_1$ is carbon.

7. A color imaging member comprising a first image-forming layer including a compound according to claim 1, said compound being in the crystalline form.

8. The imaging member as defined in claim 7 and further including a substrate and at least a second color-forming layer, said second color-forming layer being capable of forming a color different from that formed by said first color-forming layer.

9. The imaging member as defined in claim 8 and further including a third color-forming layer, said third color-forming layer being capable of forming a color different from those formed by said first and second color-forming layers.

10. The imaging member as defined in claim 9 wherein said color-forming layers form magenta, cyan and yellow color, respectively.

11. An imaging method comprising
    (a) providing an imaging member as defined in claim 7; and
    (b) converting at least a portion of said compound to the liquid form in an imagewise pattern whereby an image is formed.

12. The method as defined in claim 11 wherein step(b) comprises applying an imagewise pattern of thermal energy to said imaging member whereby at least a portion of said compound is converted to the liquid form and an image is formed.

13. The imaging method as defined in claim 12 wherein said imaging member further includes a substrate and at least a second color-forming layer, said second color-forming layer being capable of forming a color different from that formed by said first color-forming layer.

14. The imaging method as defined in claim 13 wherein said imaging member further includes a third color-forming layer, said third color-forming layer being capable of forming a color different from those formed by said first and second color-forming layers.

15. The imaging method as defined in claim 14 wherein said color-forming layers form magenta, cyan and yellow color, respectively.

16. The imaging member as defined in claim 7 wherein said compound has a melting point of from about 60° C. to about 300° C.

17. The imaging method as defined in claim 11 wherein said compound has a melting point of from about 60° C. to about 300° C.

* * * * *

UNITED STATES PATENT AND TRADEMARK OFFICE
CERTIFICATE OF CORRECTION

| | | |
|---|---|---|
| PATENT NO. | : 7,279,264 B2 | Page 1 of 1 |
| APPLICATION NO. | : 10/789566 | |
| DATED | : October 9, 2007 | |
| INVENTOR(S) | : Kap-Soo Cheon et al. | |

It is certified that error appears in the above-identified patent and that said Letters Patent is hereby corrected as shown below:

At Column 20, lines 1 and 2, Claim 1 currently reads as follows:
"alkenyl, alkynyl, substituted alkynyl, heterocycloalkyl substituted heterocycloalkyl substituted carbonyl, acy-"

At Column 20, line 2, please correct Claim 1 to read as follows:
-- alkenyl, alkynyl, substituted alkynyl, heterocycloalkyl, substituted heterocycloalkyl, substituted carbonyl, acy- --

Signed and Sealed this

Twenty-fifth Day of December, 2007

JON W. DUDAS
*Director of the United States Patent and Trademark Office*